United States Patent [19]

McAleer et al.

[11] 4,102,996

[45] Jul. 25, 1978

[54] METHOD OF PREPARING HEPATITIS B CORE ANTIGEN

[75] Inventors: William J. McAleer, Ambler; William J. Miller, North Wales; Edward H. Wasmuth, Telford, all of Pa.

[73] Assignee: Merck & Co., Inc., Rahway, N.J.

[21] Appl. No.: 789,033

[22] Filed: Apr. 20, 1977

[51] Int. Cl.[2] .......................... A61K 39/12; C12K 7/00

[52] U.S. Cl. .......................................... 424/89; 195/1.5

[58] Field of Search ............................ 424/89; 195/1.5

[56] References Cited

PUBLICATIONS

Ling et al., Hepatitis Scientific Memoranda, Jan. 1976, Memo H.

Almeida et al., The Lancet, Dec. 4, 1971, pp. 1225–1227.

Barker et al., J. of Virology, Dec. 1974, pp. 1552–1558.

Fauvel et al., Can. J. Microbiol., vol. 21, (1975), pp. 905–910.

Greenman et al., Vox Sanguinis, vol. 29, (1975), pp. 77–80.

Kaplan et al., J. Virology, vol. 12, No. 5, (1973), pp. 995–1005.

Moritsugu et al., J. of Immunol., vol. 114, Jun. 1975, pp. 1792–1798.

Tsuda et al., J. of Immunol., vol. 115, Sep. 1975, pp. 834–838.

*Primary Examiner*—Sam Rosen

*Attorney, Agent, or Firm*—Donald J. Perrella

[57] ABSTRACT

$HB_cAg$ is prepared by isolating Dane particles by isopycnic banding of fluid from $HB_sAg$ positive donors, optionally but preferably pelleting the Dane particles, and then removing the surface antigen by contacting the Dane particles with a nonionic surfactant having from about 15 to about 35 oxyethylene units in the presence of a reducing agent such as mercaptoethanol. The isolated core antigen is used as a diagnostic and immunologic agent.

7 Claims, No Drawings

METHOD OF PREPARING HEPATITIS B CORE ANTIGEN

BACKGROUND OF THE INVENTION

1. Field of the Invention

This invention relates to hepatitis B core antigen ($HB_cAg$) and, more particularly, to a process for preparing hepatitis B core antigen in high yield and purity.

Hepatitis B is one of the types of viral hepatitis which results in a systemic infection with the principal pathologic changes occurring in the liver. This disease affects mainly adults and is maintained chiefly by transfer of infection from long term carriers of the virus. Usual methods of spread are by blood transfusion, contaminated needles and syringes, through skin breached by cuts or scratches, by unsterilized dental instruments as well as by saliva, veneral contact or exposure to aerosolized infected blood.

The incubation period of type B hepatitis is relatively long: from 6 weeks to 6 months may elapse between infection and the onset of clinical symptoms. The illness usually begins with fatigue and anorexia, sometimes accompanied by myalgia and abdominal discomfort. Later jaundice, dark urine, light stools and tender hepatomegaly may appear. In some cases, the onset may be rapid, with appearance of jaundice early in association with fever, chills, and leukocytosis. In other cases jaundice may never by recognized and the patient may be aware of a "flu-like" illness. It is estimated that the majority of hepatitis infections result in a mild, anicteric illness.

Serum obtained from patients with hepatitis B infections usually contains three distinct morphologic forms. The largest of these morphologic forms, a 42-nm to 45-nm double shelled spherical particle, often referred to as the Dane particle (HBV), is believed to be the virus of hepatitis B. The outer surface or envelope of the Dane particle ($HB_sAg$) surrounds a 27-nm inner core which does not react with antibody against $HB_sAg$ and which contains a distinct antigen, the core antigen ($HB_cAg$). Antibody to $HB_cAg$ appears after acute hepatitis B infection, and also can be demonstrated consistently in chronic carriers of $HB_sAg$. Highly sensitive techniques are now available for detection of the $HB_cAg$ system. A deterrent to the more widespread use of such techniques, however, is the absence of a simple yet practical and effective method for obtaining $HB_cAg$. The methods proposed heretofore generally involve the use of selected plasma which contains exceptionally high amounts of Dane particles.

2. Objects of the Invention

It is, accordingly, an object of the present invention to provide a practical and effective method for obtaining $HB_cAg$. Another object is to provide an improved method for concentrating and purifying $HB_cAg$. Still another object is to provide a method for obtaining $HB_cAg$ from biological fluid found positive for $HB_sAg$ rather than from selected high titer $HB_sAg$ plasma. A further object is to provide immunogenic and therapeutic compositions containing $HB_cAg$. These and other objects of the present invention will be apparent from the following description.

SUMMARY OF THE INVENTION $HB_cAg$ is prepared by isolating Dane particles by isopycnic banding of biological fluid from human $HB_sAg$ positive donors, optionally but preferably pelleting the Dane particles, and then removing the surface antigen by contacting the Dane particles with a nonionic surfactant having from about 15 to about 35 oxyethylene units in the presence of a reducing agent such as mercaptoethanol.

DETAILED DESCRIPTION

The starting material for the purified hepatitis B core antigen ($HB_cAg$) of the present invention is plasma obtained from donors positive to $HB_sAg$. The plasma is obtained in conventional manner, e.g., by plasmaphoresis. The level of $HB_sAg$ may be measured in known manner by any suitable means, e.g., reversed passive hemagglutination or complement fixation. Optionally, the plasma may be cooled and the cryoprecipitate which forms is removed by light centrifugation. The Dane particles in the resulting plasma are isolated by isopycnic banding. The Dane particle-rich fraction is treated to remove Dane core antibody, preferably by pelleting, and then treated to remove the surface antigen and liberate the core antigen. Removal of the surface antigen is effected by contacting the Dane particle with a nonionic surfactant having from about 15 to about 35, preferably about 18 to about 33, oxyethylene units in the molecule in the presence of a mercaptan reducing agent, for example, mercaptoethanol, dithiothreitol, dithioerythritol, and dithiooctanoic acid. Suitable nonionic surfactants are oxyethylated alkyl phenols, polyoxyethylene sorbitan fatty acid esters, polyoxyethylene acids, polyoxyethylene alcohols, polyoxyethylene oils and polyoxyethylene oxypropylene fatty acids. Some specific examples are the following:

alkylphenoxypolyethoxy (30) ethanol
polyoxyethylene (20) sorbitan monolaurate
polyoxyethylene (20) sorbitan monopalmitate
polyoxyethylene (20) sorbitan monostearate
polyoxyethylene (20) sorbitan tristearate
polyoxyethylene (20) sorbitan monooleate
polyoxyethylene (20) sorbitan trioleate
polyoxyethylene (20) palmitate
polyoxyethylene (20) lauryl ether
polyoxyethylene (20) cetyl ether
polyoxyethylene (20) stearyl ether
polyoxyethylene (20) oleyl ether
polyoxyethylene (25) hydrogenated castor oil
polyoxyethylene (25) oxypropylene monostearate.

In isopycnic banding the partially purified concentrate is contacted with a liquid medium having a density gradient therein which includes the density of the specific antigen being isolated. The liquid medium is then subjected to ultracentrifugation to attain an equilibrium distribution of the serum components through the density gradient according to their individual densities. Successive fractions of the medium are displaced and those containing the desired antigen, i.e. the fractions having a density of from about 1.26 to about 1.30 g/cc, are separated. The concentrations of the solutions forming the gradient are selected so as to encompass the density range of from about 1.0 to about 1.41 g/cc. The liquid medium may be employed in the form of a linear gradient or a step gradient. Preferably it is employed in the form of a step gradient due to its inherently higher capacity for fractionation.

The liquid media used in the isopycnic banding step may be any density gradient in the appropriate ranges, e.g. sucrose, potassium bromide, cesium chloride, potassium tartrate, or sodium bromide. Sodium bromide is preferred.

EXAMPLE 1

A. Preparation of Dane Particles (HBV)

The rotor of a centrifuge, Electronucleonics K is filled with 8,400 ml of phosphate buffer. After running the rotor up to 10,000 rpm to degas the system, the following step gradient is pumped into the bottom of the stationary rotor:

1. 2,400 ml of 10% NaBr, $\rho = 1.08$
2. 1,000 ml of 20% NaBr, $\rho = 1.17$
3. 1,500 ml of 30% NaBr, $\rho = 1.28$
4. 3,500 ml of 40% NaBr, $\rho = 1.41$ Plasma containing $HB_sAg$, 1,750 ml, is pumped into the top of the stationary rotor displacing 1,750 ml of 40% NaBr from the bottom of the rotor. The rotor is accelerated to 30,000 rpm and run at this speed for 4 hours. The rotor is then stopped and 1,750 ml of 40% NaBr are pumped into the bottom of the rotor forcing the plasma out the top. An additional 1,750 ml of fresh plasma containing $HB_sAg$ are pumped into the top of the rotor displacing an equal volume of 40% NaBr out the bottom of the rotor. The rotor is then run at 30,000 rpm for 18 hours. After stopping the rotor 1,000 ml of Dane particle rich material in the 1.26–1.30 density region is collected.

The Dane particles (HBV) are separated from the NaBr zonal fraction in the following procedure. The zonal fraction (1000 ml) is diluted to 3000 ml using phosphate buffered saline. This material is then placed into twelve type 19 rotor plastic bottles (ea. 250 ml/bottle). The material is then centrifuged using a type 19 rotor (Beckman). The rotor is spun at 17,000 rpm (45,000 × g) for 24 hours in order to pellet the Dane particles. The rotor is then stopped and the supernate from each bottle is decanted. The pellet material from all 12 bottles is recovered in a total volume of 5–7 ml of Tris-saline buffer and stored at −70° C. This material is the Dane particle concentrate.

B. Purification of Dane Particles 1 ml of concentrated Dane particles from part A is layered over 4 ml of 20% sucrose - 1% bovine serum albumin (BSA) in Tris buffer (pH 7.6) in a SW 65 rotor with ½ × 2 inch cellulose nitrate tubes. The particles are centifuged at 35,000 rpms for 4 hours. Post centrifugation, the supernate fluid is decanted and the pellet is gently resuspended in 0.5 ml of Tris buffer with 1% BSA using a cotton tipped swab (pre-moistened with buffer). The cotton swab is then rinsed with 0.5 ml of buffer. The final volume of Dane particle material is 1 ml. The Dane particles are stored at −70° C.

C. Preparation of $HB_cAg$ (Core Antigen)

The material from part B, 1 ml, is added to 1 ml of a 1% (v/v) solution of 2-mercaptoethanol is deionized water, and 1 ml of a 1% (v/v) solution of polyoxyethylene (20) sorbitan monooleate in deionized water. The resulting mixture is agitated gently and placed in a 37° C water bath. After 1 hour the mixture is diluted with TMN-1% BSA (a solution containing 0.08 M Tris, 0.008 M $MgCl_2$ and 0.14 M NaCl, and 1% BSA) using a previously calculated quantity of diluent until if contains 32 IAHA units per ml. The solution is then dispensed into plastic 2 ml screw-cap serum tubes (0.5 ml/tube) and stored in a liquid nitrogen freezer.

EXAMPLE 2

To each of twelve 6 ml glass vials there are added 1 ml of purified Dane particles prepared as described in Example 1, 1 ml of a 1% (v/v) solution of 2-mercaptoethanol in deionized water, and 1 ml of a 1% (v/v) solution in deionized water of the materials listed below. The mixtures are agitated gently and placed in a 37° water bath. After 1 hour the resulting mixtures are assayed for $HB_cAg$ by the immune adherence hemagglutination assay.

| Nonionic Surfactant | IAHA Units |
|---|---|
| polyoxyethylene (20) sorbitan monooleate | 1000 |
| polyoxyethylene (20) sorbitan monolaurate | 1000 |
| polyoxyethylene (23) lauryl ether | 1000 |
| polyoxyethylene (20) cetyl ether | 1000 |
| alkyl phenoxypolyethoxy (30) ethanol | 1000 |
| alkyl phenoxypolyethoxy (9) ethanol | 240 |
| alkyl phenoxypolyethoxy (40) ethanol | 240 |
| polyoxyethylene (9) octaphenol | 60 |
| sorbitan monolaurate | 30 |
| sorbitan monostearate | 30 |
| sodium dodecyl sulfate | 30 |
| polyalkylaryl sulfonic acid | 30 |

The foregoing results show that nonionic surfactants containing 9 or 40 oxyethylene units are significantly inferior to those containing from 20 to 30 oxyethylene units while those without any oxyethylene units are almost totally ineffective.

EXAMPLE 3

To a first 1 ml sample of purified Dane particles from the same lot used in Example 2 there are added 1 ml of polyoxyethylene (20) sorbitan monooleate, and 1 ml of 2-mercaptoethanol. A second 1 ml sample is treated similarly except substituting 1 ml of deionized water for the 2-mercaptoethanol. Each sample is mixed, incubated for 1 hour at 37° and assayed for $HB_cAg$ by the immune adherence hemagglutination assay. The second sample without 2-mercaptoethanol is found to contain less than half the amount of $HB_cAg$ in the first sample.

EXAMPLE 4

$HB_cAg$ as prepared in Example 1 is adsorbed on alum as follows. Ten ml of $HB_cAg$ (Type Ad) containing 16–32 IA units/ml are mixed with 0.85 ml of 10% alum solution $KAl(SO_4)_2 \cdot 12H_2O$. While stirring 0.1 N NaOH is added slowly to adjust the pH to 6.8. Mixing is continued for 1 hour at room temperature. The solution is then centrifuged at 1500 × g for 10 minutes. The supernate is decanted and the pellet is resuspended with saline solution to the original volume (10 mls). The solution is then mixed for 5–10 minutes prior to use as an antigen.

EXAMPLE 5

The procedure of Example 4 is employed except using 10 ml of $HB_cAg$ (Type Ay).

EXAMPLE 6

Alum antigens prepared in Examples 4 and 5 are used to make high titer $HB_cAb$ serums. The guinea pigs are divided into two groups which are used to produce the $HB_cAb$ antiserum. The first group is administered intramuscular injections of 3 doses of 0.5 ml at monthly intervals of the product of Example 4. The second group is treated similarly with the product of Example 5. High titered hepatitis B antibody serums are produced in each group.

EXAMPLE 7

Enzyme-linked immunosorbant assay (ELISA)

The $HB_cAg$ obtained in Example 1 is purified by centrifugation on a 20–60% sucrose gradient at 200,000 × g for 2.5 hours. The $HB_cAg$ is then assayed to determine protein content.

The $HB_cAg$ is diluted to 1 μg/ml with 0.1M carbonate buffer pH 9.7 for use in the ELISA assay.

The solid phase used in the assay is a 96 well, Cooke microtiter, U-bottom, polystyrene plate.

The enzyme-conjugate is alkaline phosphatase conjugated goat anti-human immunoglobulin (Engvall et al.).[1] Use level is determined by titration.

[1]The Journal of Immunology 109, 129 (1972)

The enzyme substrate is 0.01% p-nitrophenyl phosphate in 0.1M carbonate buffer pH 9.8, containing 0.001M $MgCl_2$.

The assay method is described by E. Nassau et al.[2] This method is used to detect $HB_cAb$ in plasma and serum samples.

[2]Tubercle 57, 67–70 (1976)

EXAMPLE 8

The final product of Example 1 is treated under aseptic conditions with 1:4000 formalin at 37° C for 72 hours. Excess formalin is then neutralized with sodium bisulfite. The core antigen is then adsorbed on alum by following the procedure of Example 4.

Individuals positive for $HB_cAb$ and having an $HB_cAb$ antibody titer (as measured by the immune adherence hemagglutination assay, IAHA) of 32 IAHA units/ml or greater are administered 1 ml (40 μg) doses of vaccine intramuscularly. Additional injections are given 1 month and 3 months following the first injection. One week after the third injection the individuals are plasmapheresed and $HB_cAb$ titers are run on the individual plasma using the immune adherence hemagglutination assay. The majority of the individuals experience an increase in their $HB_cAb$ titer compared to their initial titer. Those plasmas having an antibody titer of 2000 or higher are processed to yield gamma globulin having high $HB_cAb$ titer.

EXAMPLE 9

The material from part B of Example 1, 1 ml, is added to 1 ml of a (v/v) solution of 2-mercaptoethanol in deionized water, and 1 ml of a 1% (v/v) solution of polyoxyethylene (20) sorbitan monooleate in deionized water. The resulting mixture is agitated gently and placed in a 37° C water bath. After 1 hour the mixture is diluted with SPGA using a previously calculated quantity of diluent until it contains 32 IAHA units per ml. The solution is then dispensed into plastic 2 ml screw-cap serum tubes (0.5 ml/tube) and stored in a liquid nitrogen freezer.

What is claimed is:

1. A method of preparing hepatitis B core antigen which comprises treating Dane particles with a nonionic surfactant having from about 15 to about 35 oxyethylene units in the presence of a mercaptan reducing agent.

2. A method according to claim 1 wherein the reducing agent is mercaptoethanol.

3. A method according to claim 1 wherein the nonionic surfactant is polyoxyethylene (20) sorbitan monooleate, polyoxyethylene (20) sorbitan monolaurate, polyoxyethylene (23) lauryl ether, polyoxyethylene (20) cetyl ether or alkyl phenoxypolyethoxy (30) ethanol.

4. A method according to claim 1 wherein the Dane particles are obtained by subjecting biological fluid of human hepatitis B donors to isopycnic banding in a suitable density gradient.

5. A method according to claim 4 wherein the density gradient is a step gradient and the biological fluid is plasma.

6. A method according to claim 4 wherein the density gradient is sodium bromide.

7. A method according to claim 4 wherein the Dane particles are pelleted after the isopycnic banding and before being treated with the nonionic surfactant.

* * * * *